United States Patent [19]

Wang et al.

[11] 4,051,138

[45] Sept. 27, 1977

[54] WATER-SOLUBLE AMINE-LINKED POLYMERIC COLORANTS

[75] Inventors: Patricia C. Wang; Robert E. Wingard, both of Palo Alto, Calif.

[73] Assignee: Dynapol, Palo Alto, Calif.

[21] Appl. No.: 638,730

[22] Filed: Dec. 8, 1975

[51] Int. Cl.$^2$ ................................................ C09B 5/14
[52] U.S. Cl. .................................. 260/278; 260/154; 260/156; 260/162; 260/195; 260/197; 260/42.21; 8/39 R; 260/378; 426/250; 526/23; 526/50; 8/3; 8/DIG. 7
[58] Field of Search .......... 260/278, DIG. 7, DIG. 8, 260/249, 272, 365, 367, 369, 378, 278; 426/250; 526/23, 50

[56] References Cited

U.S. PATENT DOCUMENTS

| | | | |
|---|---|---|---|
| 1,891,317 | 12/1932 | Peter | 260/278 |
| 3,920,855 | 11/1975 | Dawson et al. | 426/250 |

Primary Examiner—Lewis Gotts
Assistant Examiner—Cary Owens
Attorney, Agent, or Firm—William H. Benz

[57] ABSTRACT

Polymeric colorants comprising a hydrocarbon backbone and attached directly thereto through amine linkages, at least one water-solubilizing group and at least one optically chromophoric group are disclosed. In a preferred embodiment, the backbone is a saturated aliphatic hydrocarbon, the chromophore is an anthraquinone chromophore and the solubilizing group is a sulfonate or sulfamate residue.

21 Claims, No Drawings

WATER-SOLUBLE AMINE-LINKED POLYMERIC COLORANTS

BACKGROUND OF THE INVENTION

1. Field of the Invention

This invention relates to polymeric coloring compositions. More particularly, it relates to water-soluble polymeric colorants, especially water-soluble polymeric colorants which are nontoxic and thus are useful in edibles and their preparation.

2. Background Art

Polymeric colorants are composed of optically chromophoric groups bound to or into polymers. Such materials may be found in the prior art, for example, in Horiguchi et al. U.S. Pat. No. 3,337,288 granted on Aug. 22, 1967; in Wegmann et al. U.S. Pat. No. 3,304,297, granted on Feb. 14, 1967; in Japanese Published Patent Application 14,434, published in 1966 and cited at 66 Chemical Abstracts 19843 j; in the article by Ida et al. appearing at pages 524–30 of volume 89(4) of YAKUGAKU ZASSHI; in Kalopissis's U.S. Pat. No. 3,567,678 granted on Mar. 2, 1971; and Dawson et al. U.S. Pat. No. 3,920,855 granted Nov. 18, 1975. These and other references make it clear that in certain applications polymeric dyes can offer real functional advantages. Their larger molecular size reduces their diffisivity and increases their filmforming properties. In food coloring applications, polymeric colors can offer yet another advantage which is pointed out in the already noted Ida et al and Dawson et al references. If a polymeric color molecule has a large enough molecular weight and size, it will be too large to be absorbed from the gastrointestinal tract when eaten with food. This means that the color will not pass into the body and any risk of systemic toxicity is essentially eliminated.

In such food coloring uses and in other applications where the polymeric properties of a polymeric colorant are of importance, it is required that the chromophoric groups be stably attached to the polymer and that the polymer itself not undergo degradation under the conditions of use.

In many, if not most, applications it is desirable that the polymeric colorants be water-soluble since most substrates to be colored, especially edible substrates, contain water. One way to impart water-solubility is to incorporate water-solubilizing groups in the polymer backbone. Such an approach has the disadvantages of requiring a new backbone to be prepared each time an increase or decrease in solubility is desired and of introducing potentially liable groups into the ideally nonrupturable backbone. Another approach to imparting water-solubility is to use only chromophoric units which contain solubilizing groups — which approach limits the choice of chromophoric units which can be employed. Yet another approach involves attaching solubilizing groups to the chromophores themselves. This generally results in undesired modification and unpredictability of the color of the final polymer product.

Probably the best and most generally applicable method to prepare a water-soluble polymeric dye is to attach water-solubilizing groups and chromophoric groups directly and separately to the polymer backbone. It is to such materials that the present invention relates.

STATEMENT OF THE INVENTION

A new and advantageous form of water-soluble polymeric coloring compositions has now been found. These colorants contain one or more optically chromophoric groups covalently linked through amine linkages directly to carbon atoms of a hydrocarbon polymer backbone. Also directly covalently attached through amine linkages to this backbone but to different carbon atoms thereof, are one or more water-solubilizing groups. Polymeric colorants having this structure offer the following advantages: (1) Since the backbone of these colorants is a simple hydrocarbon backbone it is especially stable and not prone to attack or rupture under normal product handling conditions or under the conditions of metabolism nor does it interfere with the product's color properties; (2) Since the solubilizing groups are separate from and not included in the colorant groups, the degree of solubilization can be controlled independent of the tint or hue of the colorant; and (3) Since the amine linkage is an extremely stable linkage under conditions of product processing and metabolism there is essentially no risk of loss of chromophoric groups or solubilizing groups from the polymeric colorant.

In a preferred embodiment, the polymeric colorants of this invention are colorants for edibles such as foods, beverages and the like and are of a molecular size to prevent their passage through the walls of the gastrointestinal tract and hence upon consumption are essentially nonnutritive, noncariogenic, nontoxic and noncaloric.

In another apsect, this invention relates to the preparation of these colorants.

DETAILED DESCRIPTION OF THE INVENTION

The polymeric colorants of this invention consist of chromophoric groups and separate solubilizing groups both chemically (covalently) directly attached to hydrocarbon backbones through amine ( — NR — ) linkages (wherein R is hydrogen or a lower alkyl).

The Hydrocarbon Backbones

The hydrocarbon backbones employed in the present invention are olefinically saturated, that is they do not contain intentionally incorporated olefinic unsaturation. They are essentially linear, containing no appreciable long chain branching. Structurally, the backbones may be depicted as linear

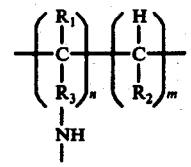

chains, wherein $R_1$ is hydrogen or a lower saturated alkyl of up to 4 carbon atoms, i.e., methyl, ethyl, propyl or butyl; $R_2$ is hydrogen, a lower saturated alkyl of up to 4 carbon atoms or an aromatic hydrocarbon of aboout 6 carbon atoms, i.e., phenyl; $R_3$ is most commonly a simple carbon to nitrogen single covalent bond but also may be a 1 to 4 carbon lower saturated alkyl bridge, or a 6 carbon aromatic (phenylene) bridge; and $n$ is an integer greater than 1 and m is at least n such that not more than ¼ the backbone carbons carry an amine group. In one other embodiment, R₃ is a methylene bridge which joins together with an adjacent R₃ into a repeating

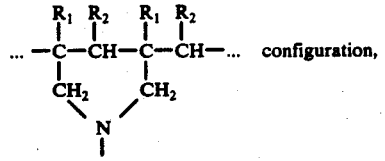 configuration, configuration, i.e, a "cyclodiallylamine" configuration. Generally, R₁ is preferred to be hydrogen or methyl and R₂ is preferred to be hydrogen or methyl. The backbone may comprise added copolymeric units as well. These units need not be solely hydrocarbons but should only add hydrocarbon to the structural chain of the backbone. The added units include, for example, the hydrocarbons

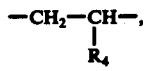

wherein R₄ is hydrogen, a 1 to 4 carbon alkyl or an aryl, alkarly or aralkyl of from 6 to 8 carbons; the oxyhydrocarbons

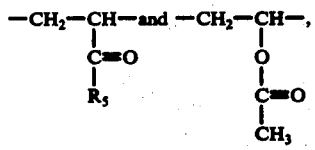

wherein R₅ is hydrogen, a 1 to 4 carbon alkyl, a —O—CH₃ group, or an —NH₂ group; and the nitrilohydrocarbon

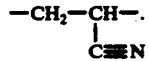

As is illustrated by these formulae, the sole contribution made to the backbone chain by these materials is hydrocarbon.

The following is a list of exemplary homopolymeric backbones for use in the colorants of this invention. It will be appreciated that the aforementioned copolymeric groups could be incorporated also. Suitable backbones include poly(vinylamine),

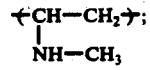

poly(N-methylvinylamine), $\begin{array}{c} +\text{CH}-\text{CH}_2\!\!\rightarrow; \\ | \\ \text{NH}-\text{CH}_3 \end{array}$ poly(α-methylvinylamine)

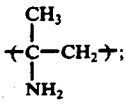

poly (β-methylvinylamine),

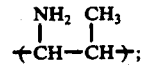

poly(α-ethyl-, α-propyl-, or α-butylamine,

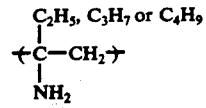

and the like.

Preferred homopolymers include poly(vinylamine), poly(N-methylvinylamine), and poly(α-methylvinylamine). The length (or size) of the backbone chain is of importance. Clearly, since at least one chromophoric group and at least one water-solubilizing group are attached to the backbone through amine linkages, the backbone must contain at least two such amines. If one is to obtain most advantageous polymer properties with the polymeric colors of this invention, n, that is the number of amine groups on a polymer chain, should be at least 20. However, if n is substantially greater than about 3000, say 5000 or 10,000, generally the performance as colorants of the final polymers decreases. Thus a preferred size of backbone obtains when n is between 20 and 3000 more preferably when n is betweem 40 and 2000 and most preferably when n is between 100 and 1500.

When experimental molecular weights are noted herein they have been derived by gel permeation techniques. In the primary technique, a silanized porous glass support is used with 0.01 m LiBr in DMF eluent. Detection is by refractometer with standardization being based on purchased polystyrene standards. Expressed in terms of molecular weight, examples of backbones meeting the general size criteria (n = 20 to 3000) include poly(vinylamine) of molecular weight 860 to 129,000; poly(α,β or N-methylvinylamine) of molecular weight 1180 to 17,000 and poly(αor β-butylvinylamine) of molecular weight 2020 to 303,000. In the same terms, backbones meeting the most preferred size criteria (n = 100 to 1500) include poly(vinylamine) of molecular weight 4300 to 64,500 and poly (α-methylvinylamine) of molecular weight 5900 to 88,500. Further preferences in molecular size will be noted when the colorant products are to be used as colorants for edible compositions. These will be set forth hereinafter.

The backbones are generally prepared separately prior to chromophore and solubilizer attachment. This may be done by free radially polymerizing olefinically unsaturated amine- or amine-precursor-substituted monomers. A number of representative backbone preparations are depicted herein in Examples I — VI. Alternative preparations are set forth at Kurtz and Disselnkotter, U.S. Pat. No. 3,424,791; Hanford and Stevenson, U.S. Pat. No. 2,276,840; Hanford and Stevenson, U.S. Pat. No. 2,231,905; Horwitz and Aschkenasy, Belg. 637,380; Hart, *Makromol. Chem.*, 32, 51(1959); Hart, *J. Polymer. Science*, 29, 629 (1958); Blomquist, et al., *J. Am.*

Chem. Soc., 67, 1519 (1965) Kurtz and Disselnkotter, Liebigs Ann. Chem., 764, 69 (1972); Bailey and Bird, J. Org. Chem., 23, 996 (1958); and Seki et al., Chem. Pharm. Bull., 20, 361 (1972); which disclosures are expressly incorporated by reference into this patent application.

The Amine Linkages

The amine linkages which serve to covalently attach the chromophoric groups and water-solubilizing groups to the backbone may be secondary amines, that is,

They also may be lower saturated alkyl-substituted tertiary amines, that is,

amines, wherein R is a lower saturated alkyl of from one to four carbons, e.g., a methyl-, ethyl-, propyl-, or butyl-substituted amine. The secondary amine linkage is generally preferred. Combinations of two or more amine linkages may be employed as well. The amine linkage is attached directly to the hydrocarbon backbone via a nitrogen-to-backbone-carbon covalent bond. The amine linkages also attach directly to the chromophoric groups or to the water-solubilizing groups via covalent bonds.

The Chromophoric Groups

The chromophoric groups employed in the present coloring compositions are organic optical chromophores. These materials are defined to be organic chemical groups which exhibit a visual color to the human eye when attached to polymeric backbone via amine linkages. These chromophores can be selected from a wide range of classes of groups, including the azo chromophores, anthraquinone chromophores, xanthene chromophores, triphenylmethane chromophores, indigoid chromophores and the like. These classes of chromophores are merely representative — other similar materials also being usable. Among these chromophores special preferences are given to azo chromophores, because of the great variety of technically important clear intense red to yellow colors which they enable and to anthraquinone chromophores because of their great stability under stressful conditions of heat and light and the wide range of colors which they permit. Among chromophores, those which are themselves water-insoluble generally achieve most improved usefulness when used in the present polymeric form. A chromophore is defined as being water-insoluble if its solubility in room temperature water at neutral conditions (pH 7) is less than 500 parts per million weight (basis water). Conversely, the polymeric colorants of this invention are water-soluble, which property is defined to mean that such a polymeric color exhibits a solubility in neutral room temperature water of greater than 500 parts per million weight (basis water).

Preferred anthraquinone chromophores in their unattached (monomeric) state have a leaving group such as a —Cl, —Br, —I, —SO$_3$Na, —N$_2^{30}$Cl$^{31}$, or —NO$_2$ group attached to their aromatic ring. This permits the chromophore's facile attachment to the backbone amines by the known technique wherein copper is used to catalyze the leaving groups' displacement by amines. In many cases, no catalyst is required to effect the desired displacement. Several classes of anthraquinone chromophores deserve special mention: Aminoanthraquinone chromophores of the structure of Formula I;

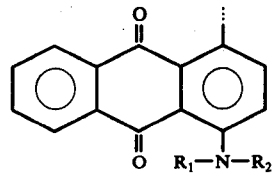

I

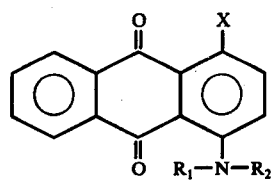

IA formed by coupling the monomer IA wherein R$_1$ is a hydrogen or a lower saturated alkyl of up to four carbon atoms, R$_2$ is hydrogen, a lower saturated alkyl of up to four carbon atoms or an aryl or alkaryl of from six to eight carbons and X is a leaving group. These are useful to give the range of blue colorants listed in Table I.

TABLE I

| Compound | | |
|---|---|---|
| R$_1$ | R$_2$ | Color |
| hydrogen | hydrogen | purplish blue |
| hydrogen | methyl | greenish blue |
| hydrogen | ethyl, propyl or butyl | greenish blue |
| hydrogen | aryl | navy blue |

Anthrapyridones of the structure of Formula II;

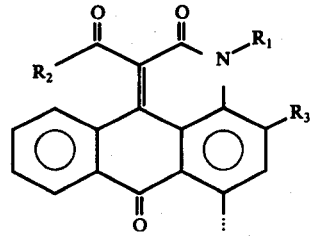

II

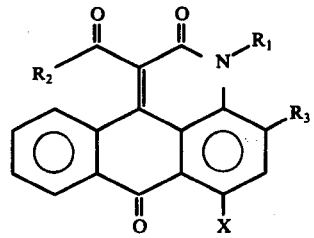

IIA formed by coupling the corresponding monomer, wherein X is a leaving group, R$_1$ is hydrogen, a lower saturated alkyl of from 1 to 4 carbon atoms inclusive, or an aryl grouping of about 6 carbons, R$_2$ is a 1 to 4 carbon lower saturated alkyl, a 1 to 4 carbon lower saturated alkoxy, or an aryl grouping of about 6 carbon atoms, and $R_3$ is hydrogen or a 1 to 4 carbon lower saturated alkyl. These chromophores are rich reds. Preferred among the anthrapyridones are these according to Formula II wherein $R_1$, $R_2$, and $R_3$ are as shown in Table II.

TABLE II

| $R_1$ | $R_2$ | $R_3$ |
|---|---|---|
| hydrogen | 1-4 carbon alkyl | 1-4 carbon alkyl |
| hydrogen | methyl | methyl |
| hydrogen | methoxy | 1-4 carbon alkyl |
| hydrogen | methoxy | methyl |
| hydrogen | ethoxy | 1-4 carbon alkyl |
| hydrogen | ethoxy | methyl |
| hydrogen | phenyl | methyl |
| methyl | methyl | hydrogen |
| methyl | phenyl | hydrogen |
| ethyl | methyl | hydrogen |
| methyl | methoxy | hydrogen |
| ethyl | methoxy | hydrogen |

Anthrapyridines of the structure of Formula III:

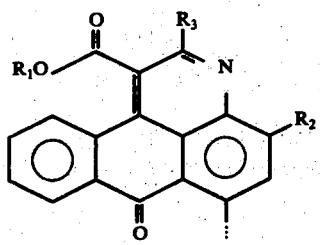

III which are formed by coupling the corresponding monomeric chromophore

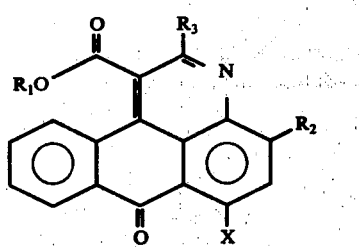

IIIA wherein X is a leaving group, $R_1$ is a 1 to 4 carbon lower alkyl group or aryl grouping of about 6 carbons, $R_2$ is hydrogen or a 1 to 4 carbon lower alkyl, and $R_3$ is a 1 to 4 carbon alkyl group or aryl grouping of about 6 carbons. These colorants range in hue from yellows to reds to brown. Preferably $R_2$ is hydrogen or methyl. pyridinoanthrone dyes of the structure of Formula IV;

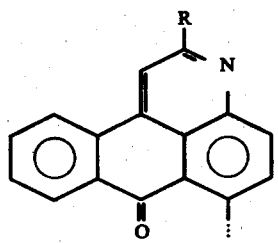

IV

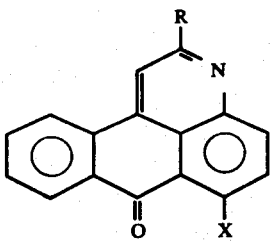

IVA may also be used. These are formed by coupling the corresponding monomeric chromophore wherein R is hydrogen or a 1 to 4 carbon saturated alkyl.

Anthrapyrimidines of the structure of Formula V;

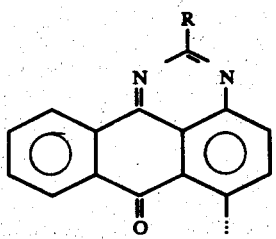

V formed by coupling the monomeric chromophores of the formula

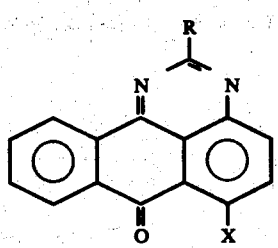

VA wherein R is hydrogen, a 6 carbon aryl, a 1 to 4 carbon saturated alkyl or a halogen as described in U.S. Pat. No. 1,947,855 which deals with monomeric colorants. These materials are reds and yellows.

Anthrapyrimidones of the structure of Formula VI;

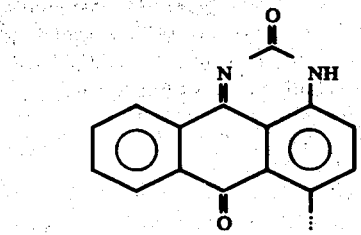

VI formed by coupling the monomeric chromophores.

VIA

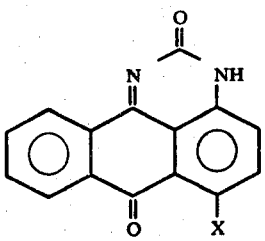

These materials are violets. Substitution of 4 position by amino group gives violet dye (U.S. Pat. No. 1,004,107). Hydrogen in the 4 position is greenish yellow.
Anthraquinones of the structure of Formula VII;

VII

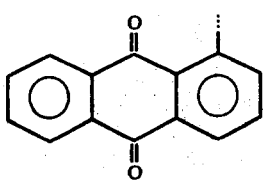

formed by coupling the monomeric chromophores.

VIIA

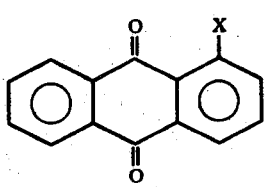

These materials are reds.
Anthrapyridones of the structure of Formula VIII;

VIII

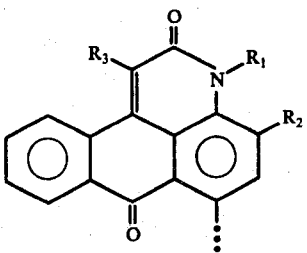

formed by coupling the monomeric chromophores,

VIIIA

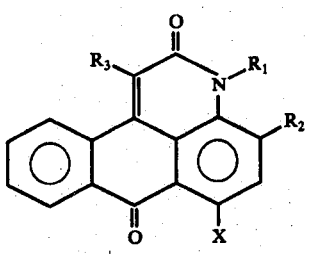

wherein $R_1$ is hydrogen or methyl, $R_2$ is hydrogen or 1 to 4 carbon lower alkyl and $R_3$ is hydrogen, a halogen (i.e., Br or Cl), cyano (i.e., —CN), $NO_2$ or a lower alkyl of 1 to 4 carbon atoms.

Among the azo colorants, those having monomeric forms with a sulfonyl chloride comprise one preferred group since they may be easily attached to the amine backbone via the well known Schotten-Baumann reaction. Exemplary chromophores of this class and their chloro precursors include the first 4 materials shown in Table III. Also listed in Table III, are several nonazo chromophores which are attached via the Schotten-Baumann reaction.

Table III

| Chromophore | Precursor |
| --- | --- |
| (Orange) | |

Table III-continued

| Chromophore | Precursor |
|---|---|
| (Yellow) phenylsulfonyl-azo-pyrazolone (HO, CH₃, phenyl) | (Precursor) with ClSO₂ and AcO instead of HO |
| (Red) naphthylsulfonyl-azo-naphthol (OH) | (Precursor) with ClSO₂ and OAc |
| (Burgundy) phenylsulfonyl-azo-dihydroxynaphthalene (HO, HO) | (Precursor) with ClSO₂ and AcO, AcO |
| (Red) anthrapyridone with SO₂⁻ substituent (R₁, R₂, R₃, R₄) | (Precursor) with SO₂Cl substituent |

$R_1$ = H, or 1 to 4 C alkyl $R_2$ = H, or 1 to 4 C alkyl $R_3$ = 1 to 4 C alkyl or alkoxy $R_4$ = 1 to 4 C alkyl or alkoxy

Table III-continued

| Chromophore | Precursor |
|---|---|

(Structures shown, with labels:)
- (Red)
- (Yellow)
- (Yellow)
- (Yellow)
- (Blue)
- (Yellow)

$R_1$ = $CH_3O-$, $CH_3S-$, or Br

Table III-continued

| Chromophore | Precursor |
|---|---|

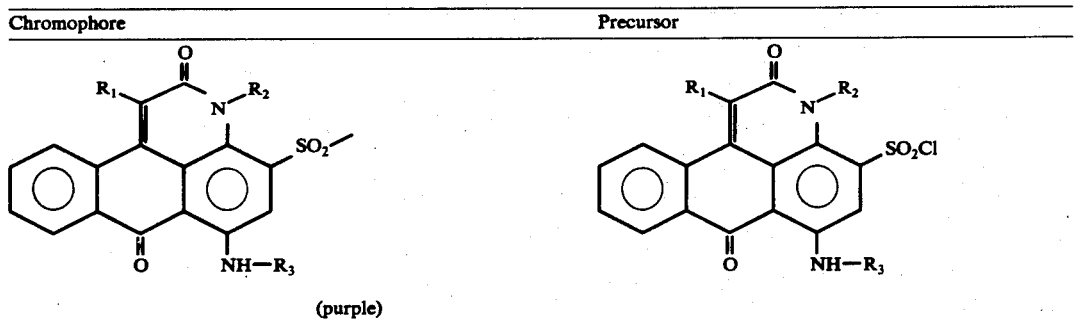

(purple)

$R_1$ = H, $CO_2$-1 to 4 carbon alkyl or CO-1 to 4 carbon alkyl
$R_2$ = H or 1-4 carbon alkyl

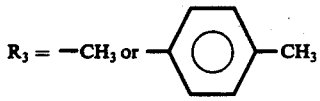

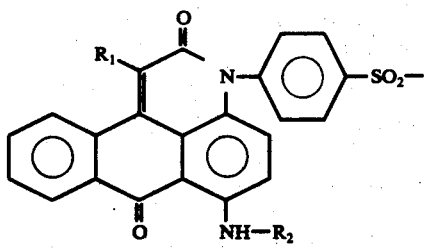 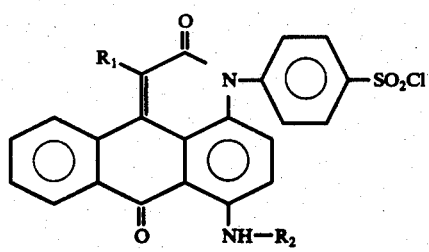

Red as shown in Brit. Patent 525,091 (1941)

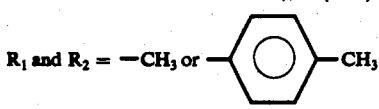

The Solubilizing Groups

Also covalently attached directly to polymer backbone amine groups are water-solubilizing groups. Any group which, when attached to the polymer, increases the polymer's hydropillicity or solubility in water may be used and is included within the definition of a solubilizing group. Generally, suitable solubilizing groups can be further characterized as containing a sulfur oxide group such as an alkyl sulfonate group, a sulfonate group or the like. Preferred among solubilizing groups are the $-SO_3^-$ group; the $-R_s-SO_3^-$ and $-SO_2-R_s-O-SO_3^-$ groups, $R_s$ is a 2 to 4 carbon alkyl, and the $-SO_2-R_9-SO_3^-$ group wherein $R_9$ is a 2 carbon alkyl. These groups when directly attached to backbone amines, respectively, assume the structures:

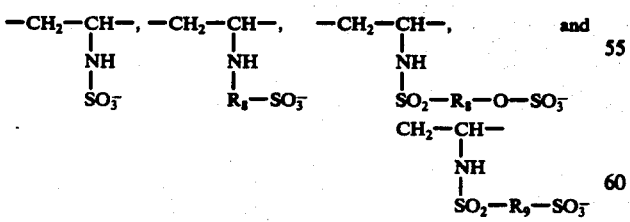

The $-SO_3^-$ groups may be introduced easily by contacting the amine group-containing polymer, generally after chromophore attachment, with sulfur-trioxide in one of its commercially available stabilized forms such as with pyridine or with a lower trialkyl amine such as triethyl or trimethyl amine.

The $-R_s-SO_3^-$ groups are introduced by contacting the amine group-containing polymer either before, after, or intermediate chromophore attachment, with an amine alkylating sulfonate, such as propane sultone, butane sultone, or the like. Also, by nucleophilic displacement reactions with β-substituted ethane-sulfonic acid salts such as $X-CH_2-CH_2SO_3Na$ where X = Br, Cl, I, OMe, or $-OSO_3^-$.

The $-SO_2-R_9-SO_3^-$ and $-SO_2-R_s-O-SO_3^-$ groups are added by contacting the amine group-containing polymer with carbyl sulfate or the like under the conditions set forth in Belgian Patent 620,445 dated Jan. 21, 1963, which patent is herein incorporated by reference.

Relative Proportions of Solubilizing Groups and Chromophores

The compositions of this invention may be represented by the following general structural formula:

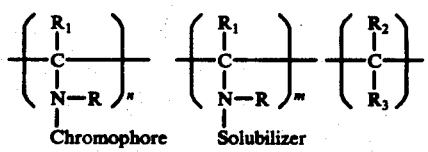

wherein R is hydrogen or a lower alkyl, $R_1$, $R_2$, and $R_3$ are hydrogens or lower alkyls, and the C's are backbone carbon atoms. As a rule, not more than one-half the backbone carbon atoms but at least about one-eighth of the backbone carbon atoms carry an amine group. A portion (n) of these amines carry optically chromophoric groups while a portion (m) carry solubilizers. $n$ equals from about 0.2 to about 4 times $m$. Preferably, $n$ equals from 0.4 to 2 times $m$. These values are dictated by several considerations. If $n$ is less than about 0.2 times $m$, the color strength of the polymeric colorant is too low. If $n$ is greater than about 4 times $m$, the resulting product will often lack adequate solubility in water and aqueous media. Similarly, if less than about one-eighth the backbone carbons carry amine groups, the color will be too weak, i.e, too much of the polymeric molecule will be nonchromophoric. If greater than one-half the backbone carbons carry an amine group, there is too great a tendency for interaction among the pendant chromophores and the solubilizer groups.

Preparation of the Compounds

Conceptually, the compounds of this invention can be prepared by the following basic routes:

1. An N-vinylamine-substituted chromophore can be polymerized with a N-vinylamine-substituted solubilizer group under free radical conditions to yield the desired solubilized product.
2. An N-vinylamine-substituted chromophore precursor can be copolymerized with an N-vinylamine-substituted solubilizer group under free radical conditions to yield a polymer product which can be further processed to yield the desired solubilized polymeric colorant.
3. A preformed backbone can be treated to attach solubilizers and then to attach chromophores.
4. A preformed backbone can be treated to attach chromophore precursors and then to attach solubilizers and finally to convert the precursors to chromophores.
5. A preformed backbone can be treated to add chromophores and thereafter treated to attach solubilizers.

Of these routes, the last is the most preferred. The first two routes suffer the disadvantage of not permitting the close control of molecular size which is achieved when a separate purified backbone is used. The third route gives excellent results when the amines of the uncombined backbone are secondary amines since it is only possible for a solubilizer or a chromophore and not both to be attached to a single amine group. When a primary amine containing backbone is employed it is likely that there will be a mixture of single and double attachment to a single amine. If the color of the chromophore is dependent upon this double vs single attachment — there may be problems with the predictability of the material's exact color. The fourth route eliminates this problem and can be useful. The fifth route, because of the relatively high degree of selectively which can be obtained with solubilization group attachment, is generally preferred.

When this last route is followed, this first step involves obtaining an amine group-containing polymer backbone. In the case where poly(vinylamine) is the backbone a full disclosure of one route to the polymer is given in U.S. Application Ser. No. 520,530 filed Nov. 4, 1974 U.S. Pat. No. 4,018,826 by Glass et al., which application is herein incorporated by reference, and which route is exemplified herein as Example 1. In the case where the backbone is a poly(N-alkyl-vinylamine) such a material can be prepared by first reacting the corresponding N-alkylaminoethanol with an excess (preferably from 2 to 3 equivalents) of an acid anhydride, preferably acetic anhydride, at an elevated temperature, especially 75°-140° C, to yield in 5-60 minutes the bis-acetate product which in the case where acetic anhydride is used has the formula

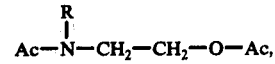

R is lower N-alkyl such as methyl and "Ac and OAc" are halves of the added acetic anhydride. The bis-acetate product is pyrolyzed in vapor phase at 350°-600° C to yield N-alkylvinylacetamide. The N-alkylvinylacetamide may be purified, by distillation or crystallization, and then polymerized in liquid phase in the presence of a suitable free radical initiator such as benzoyl hydroperoxide, other organic peroxides or other initiators such as AIBN or the like. This polymerization is generally carried out at a temperature of from 40°-100° C and at a catalyst level of from 0.5–10% mole. It is generally carried out in a suitable organic liquid solvent, especially a lower alkanol, such as methanol, ethanol, or isopropanol. The resulting poly(N-alkylvinylamide) is then hydrolyzed by contact with an excess of a mineral acid, such as sulfuric hydrochloric, perchloric or the like. This reaction is slow, requiring temperatures of at least 80° C and as high as 175° C and times of from 20-100 hours to go to completion. The hydrolysis product is the desired poly(N-alkylvinylamine) as the corresponding acid salt.

Once the backbone of choice is at hand, the next step in the preparation of the present compounds is to attach the chromophores. As pointed out in the description of suitable chromophores, there are several routes which find excellent application with certain classes of chromophores. For example, in the case of anthraquinone chromophores, it is possible to effect facile attachment by employing an anthraquinone bearing a leaving group attached to its aromatic ring. This leaving group is readily displaced by the backbone amine, generally in the presence of a copper catalyst, such as copper metal, cuprous oxide, copper I salts (cuprous chloride, etc), copper II salts (cupric acetate, etc.) and complexes of copper and copper oxides or salts with a carbon carrier. One pecularity of this reaction is the general need to employ an alkanol cosolvent, such as methanol, ethanol, isopropanol, β-methoxy ethanol, diethylene glycol, or ethylene glycol with an about 2:1 to about 1:2 proportion of water.

This reaction is generally carried out at an elevated temperature, such as from about 80° C to about 130° C, with the solvent reflux temperature often being most convenient. Following reaction, it is best to filter the reaction mixture to remove solid catalyst which could interfere in later steps.

When an azo chromophore is used, it is useful to employ a chromophore bearing a sulfonyl halide group or a methyl halide group especially a methyl chloride or bromide group. These functionalities react with the amine backbone in the presence of base at pH 10-11 to form the desired couple. This reaction is often referred to as the Schotten-Baumann reaction and goes smoothly at temperatures of from 0° to 60° C and requires from about 2 to 12 hours to complete. In the case of azo compounds, it should be remembered that the polymer backbone with its amine groups could interfere with an attempt to diazotize an attached azo dye precursor. Thus, it is best when azo colors are involved to attach a diazotized color unit, rather than an undiazotized azo color precursor.

Following chromophore attachment, the $SO_3^-$—containing solubilizing group, is attached under sulfamation conditions. This involves, in the case of $SO_3^-$ addition, contacting the polymeric colorant with an organic amine —$SO_3$ complex (1 to 4 equivalents of $SO_3$ per equivalent of residual amine, preferably 1.1 to 3 equivalents) at a temperature of from 10° C to 150° C, especially 25° C to 125° C for a period of 24 hours to 0.2 hours, especially 24 hours to 2 hours. The pH should be kept in the basic range such as from pH 7 to 13, especially pH 8-12. This solubilization is suitably carried out in water.

Use of Colorants

The colorants of this invention, being water-soluble, find wide applications in the coloring or tinting of water-solvented or water-containing materials such as water-based paints and inks, hydrophilic polymers, and the like. In an especially advantageous use, these colorants are admixed with edible materials, such as foods, beverages, medicines and the like. In this use it is most useful to size the colorants such that their molecular weight is not less than about 1500, preferably from 2000 to 200,000. Most preferably from 5,000 to 150,000. A colorant of this molecular weight has a molecular size which is too large to permit its absorption through the walls of the gastrointestinal tract and thus any risk of systemic toxicity arising from absorption of colorant from the gastrointestinal tract is eliminated. The colorants, because of their carbon-carbon backbone and direct amine linked chromophores, are essentially free of degradation at the conditions of passage through the gastrointestinal tract.

In nonedible applications, the colors of this invention may be used alone or may be admixed with other colorants in amounts of from about 20 ppm to 10% by weight in water-based paints, in water-soluble inks and dyes and may be applied to fibers, fabrics, paper and the like.

In applications with edible materials, the colorants are added in an effective coloring amount, say from about 10 ppm to about 1% by weight (preferably from 10 to 1000 ppm) to foods such as gelatin desserts, dispersed in dry cake mixes and cereals, added to fruits and other canned foods, to beverages such as carbonated beverages, for example orange, grape and cherry soda wines and the like; and added to medicines such as cough elixers, cough drops and diverse other usually colored medicaments for man or beast alike. These applications involve the art known procedures of dispersing, dissolving or otherwise spreading the colorant upon or through the object to be colored.

The invention will be further described by reference to the following examples. These are intended to provide an understanding of specific embodiments of the invention and are not to be construed as limiting the invention's scope.

EXAMPLE I

Preparation of poly(vinylamine) backbone:

A. Preparation of Vinylacetamide

To 2304 g of acetamide (technical) in a 12 liter reaction flask was added 62.2 ml of 6M aqueous sulfuric acid followed immediately by 661 g of acetaldehyde (99+%). This mixture was stirred and heated until the internal temperature reached 78° C (11 minutes) at which point the clear solution spontaneously crystallized, causing a temperature rise to 95° C. The reaction product, ethylidene-bis-acetamide, was not separated. Heating and stirring were continued for another 5 minutes to a temperature of 107° C and a mixture of 150 g calcium carbonate (precipitated chalk) and 150 g of Celite$^R$ diatomaceous earth powder was added. A first distillate fraction of water and acetamide was removed. The remaining material was transferred to a 22 liter flask and cracked at 35 mm Hg and 185° C. A fraction made up of vinylacetamide and acetamide, was taken overhead and pooled with seven other previously prepared batches. This pooled material was analyzed by NMR and found to contain 5.77 kg of vinylacetamide and 2.45 g of acetamide.

B. Polymerization of Vinylacetamide

The vinylacetamide-acetamide mixture of Part A was mixed with 4.1 l of isopropanol and chilled overnight. Crystallized acetamide was removed by filtration. The filtrate plus rinses were diluted to a total isopropanol volume of 30.58 l. This solution was placed in a 50 l flask, deoxygenated and heated to 88° C. Then a solution of 233 g of AIBN polymerization catalyst in 830 ml of acetone was added and the mixture was stirred at temperature for about 4 hours to complete polymerization. The resulting thick solution was stripped of solvent to a volume of 15.3 liters and then poured into 95 l of stirred acetone. The polymer formed a precipitate which was recovered by filtration, rinsed with acetone, and dried at 50° C in a vacuum oven. The final product was 5 kg of poly(vinylacetamide) of a molecular weight of 30,000.

C. Hydrolysis of Poly(vinylacetamide) to Poly(-vinylamine hydrochloride)

The poly(vinylacetamide) obtained in Part B (4.97 kg) was dissolved in 5.85 l of water with heating in a 50 l flask. Concentrated hydrochloric acid (5.85 l) was added and the resulting solution was stirred and heated at a gentle reflux (97°-106° C) for 23 hours. A precipitate formed and was redissolved by addition of 1,170 ml of water. Reflux was continued and over the next 17 hours, 1,000 ml of water was added in several portions to maintain solubility of the polymer. After a total of 40 hours at reflux, the polymer was precipitated by the addition of 5.85 l of concentrated hydrochloric acid. A thick polymeric gum was isolated by decantation and dried under vacuum at 50°-100° C with occasional pulverization for 56 hours to give 3.1 kg of poly(vinylamine hydrochloride) as a granular solid.

EXAMPLE II

Preparation of poly(N-methylvinylamine):

A. Formation of bis-acetylate

The preparation of poly(N-methylvinylamine) was begun by adding 250 g of N-methylaminoethanol to 691 g (2.20 equivalents) of acetic anhydride at 115°-120° C. The reaction was very exothermic (cooling required) and was complete by the time the addition was concluded. The bis-acetylated product,

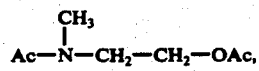

was isolated by vacuum distillation (bp 95°-98° /0.1 mm) as a colorless oil in 93% yield.

B. Pyrolyses of bis-acetylate

The bis-acetylated product of Step A was pyrolyzed by passing 642 g of this material at a rate of 1.17 g/min through a Pyrex[R] helices-packed quartz tube (3.5 cm diameter, 40 cm length) maintained at 480°. A 400 ml/min argon stream was employed. The crude pyrolysate was a dark orange oil weighing 629 g. The crude mixture containing the desired N-methylvinylacetamide was distilled (72° C/20 mm) to afford 119 g (30%) of purified N-methylvinylacetamide.

C. Polymerization

Polymerization of 75 g of purified N-methylvinylacetamide was carried out in 150 ml of methanol at 70° C in the presence of 4 mol % of AIBN. The polymerization was complete within 12 hours and afforded 72 g (96% yield) of poly(N-methylvinylacetamide).

D. Hydrolysis

The polymeric amide of Step C was hydrolysed with 6N HCl at 125° to yield poly(N-methylvinylamine) as the hyrochloride. This material had a molecular weight of about 20,000 as determined by gel permeation chromotography comparisons to standards. The hydrolysis was monitored by NMR and required roughly 40 hours to go to completion. The product was isolated in essentially quantitative yield by precipitation of the partially evaporated reaction mixture from isoporpanol.

EXAMPLES III AND IV

Preparation of high and low molecular weight poly(vinylamine hydrochloride):

The polymerization of vinylacetamide set forth in Step B of Example I was repeated twice on a smaller scale and varying reaction conditions to change the product molecular weight.

In Example III, the relative amount of AIBN polymerization catalyst was reduced by a factor of four, the reaction temperature was lowered to 63° C and the reaction time was increased to 87 hours. The product was recovered as in Example I, Step B and found to have a molecular weight of 110,000. This material was hydrolyzed to poly(vinylamine) hydrochloride by the method of Example I, Step C.

In Example IV, the relative volume of isopropanol solvent employed was doubled. This reduced the average molecular weight of the poly(vinylacetamide) product to 20,000. The poly(vinylacetamide) was hydrolyzed to poly(vinylamine) in accordance with the process of Example I, Step C.

EXAMPLE V

Preparation of poly($\alpha$-methylvinylamine):

A. Preparation of 2-Amino,2-Cyano-Propane 85.1 g (1 mole) of acetone cyanohydrin is placed in a 2 l pressure vessel and the temperature is raised to 75° C. The pressure is raised to 25 psi with $NH_3$ gas and is maintained there until the pressure no longer drops (approximately 45 minutes). The crude product is then distilled to afford 46.5 g (0.55 mole, 55%) of product as a colorless oil, bp 58°–60°/20 mm.

B. Preparation of 2-Acetamido-2-Cyano-Propane 46.0 g (0.55 mole) of the aminonitrite is added to 67 g (1.20 equiv.) of $Ac_2O$ with stirring at 80°. After 10 minutes the crude product is vacuum distilled to afford 55.9 g of a yellow solid, bp 115°/0.20 mm.

Recrystallization from benzene affords (48.3 (0.38 mole, 70%) of cream colored needles.

C. Preparation of Isopropenyl Acetamide

Pyrolysis of the acetamido nitrile is carried out by passing 27.6 g (0.22 mmole) through a 4 mm Pyrex[R] helix packed quartz column maintained at 600°. The column employed is 3.5 cm in diameter and 40 cm in length. The addition is carried out under a vacuum of 15 mm and the HCN generated is collected in a liquid $N_2$ trap. The product is 17.5 g of dark yellow solid. Distillation affords 10.4 g (0.10 mole, 48%) of product as a pale yellow crystalline solid, bp 72°–76°/0.20 mm.

D. Preparation of Polyisopropenyl Acetamide 5.0 g (43.9 mmole) of 89% pure isopropenyl acetamide is refluxed for 60 hours under Ar in 15 ml of MeOH containing 144 mg of AIBN. The product is isolated by precipitation from acetone to afford 1.39 g (28%) of a white powder. The molecular weight is 2,000.

E. Preparation of Polyisopropenyl Amine 300 mg (3.03 mmole) of the above material is refluxed for 24 hours in 20 ml of 6N HCl under Ar. The reaction solvent is removed to afford 0.42 g of product. Analysis indicated it to be 73% deacetylated.

EXAMPLE VI

Preparation of Poly(N-butyl vinylamine):

A. Formation of bis-acetate 117 g (1 mole) of N-n-butylaminoethanol is treated with 225 g (2.2 mole) of $Ac_2O$ at 100° for 4 hours. The bis-acetate is obtained by vacuum distillation in about 82% yield.

B. Pyrolysis of bis-acetate

The bis-acetate product of Step A is pyrolysed by passing 100.5 g (0.5 mole) of this material at a rate of 1.25 g/min through a Pyrex[R] helices-packed quartz tube (3.5 cm × 40 cm) maintained at 495°. A 400 ml/min Ar stream is employed. The crude pyrolysate is a brownish-orange oil weighing 87.3 g. The crude mixture containing the desired N-n-butylvinylacetamide is distilled (96°/20 mm) to afford 30.3 g (43%, 0.22 mole) of product.

C. Polymerization

A sample of 25.0 g (0.18 mole) of purified vinylacetamide from Step B above is polymerized in 60 ml of MeOH at reflux in the presence of 4 mole % AIBN. The polymerization is complete within 18 hours and afforded 23 g (92%) of poly(N-n-butylvinylactamide). The product is isolated by precipitation from ether and the molecular weight is determined to be about 38,000.

D. Hydrolysis

The polymeric amide of Step C is hydrolyzed with 10 parts by weight of 6N HCl at 125°. The yield of poly(N-n-butylvinylamine) as the hydrochloride salt is quantitative. The hydrolysis, which is monitored by NMR, requires about 60 hours to reach completion. The product is isolated by precipitation of the partially evaporated reaction mixture from isopropanol.

EXAMPLE VII

Preparation of a Red Colorant:

A. Preparation of 1-nitro-2-methylanthraquinone

To a 1 liter flask was added 100 g (0.45 mole) of 2-methylanthraquinone and 500 ml of 96% $H_2SO_4$. The mixture was stirred until it was entirely homogeneous and then cooled to 0° C. The addition of 50.5 (0.50 mole) of $KNO_3$ was then carried out in ten portions in such a way that the temperature did not rise above 5° C. This required two hours. A yellow product precipitated out after roughly half the $KNO_3$ has been added.

The yellow slurry was then stirred at 0° C for 20 hours and poured into 12 l of ice/H₂O with vigorous stirring. Stirring was stopped, the precipitate was allowed to settle, and the liquid was removed. The precipitate was washed with water until the pH of the wash water was pH 4-5.

An aqueous slurry of the precipitate (2.5 liters in volume) was placed in a 5 liter flask. 100 g of Na₂SO₃ was added and the mixture was heated and stirred at 95° C for three hours. The slurry was filtered. The solids were washed with boiling H₂O and sucked dry. The product was shown to be 1-nitro-2-methylanthraquinone.

B. Preparation of 1-amino-2-methylanthraquinone

The wet filter cake of 1-nitro-2-methylanthraquinone (0.45 mole) was placed in a 5 l flask. To the flask was added 420 g (1.75 mole) of Na₂S·9H₂O dissolved in 2.5 l of H₂O and the slurry was heated and then stirred at 95°-99° C for 2 hours. The reaction mixture was filtered and the orangish-red solid 1-amino-2-methylanthraquinone product was washed with hot H₂O until the filtrate was clear and dried in vacuo at 70° C.

C. Preparation of 1-amino-2-methyl-4-bromoanthraquinone

Into a 250 ml flask was added 10 g (42.2 mmole) of 1-amino-2-methylanthraquinone of Part B and 150 ml of glacial acetic acid. The mixture was heated to 35° C and 8.44 g (52.8 mmole) of bromine was added in one portion. After stirring for 20 hours at 35° C, TLC (CHCl₃ on SiO₂) showed 10-20% of residual starting material still remaining.

An additional 1.69 g (0.25 equivalent) of Br₂ was added and the temperature was raised to 50° C for 4 hours. TLC at this time indicated that the reaction was essentially complete.

The reaction mixture was cooled to room temperature and filtered. The solid product was washed with acetic acid (50 ml) and H₂O (100 ml).

The wet filter cake was added to 500 ml of hot (80° C) H₂O containing 25 g of NaHSO₃ and stirred for 30 minutes at this temperature. The red solid 1-amino-2-methyl-4-bromoanthraquinone was recovered, washed and dried.

D. Preparation of 3'-carbethoxy-2-methyl-4-bromo-1,9-anthrapyridone

With magnetic stirring, two mmoles (630 mg) of the bromoanthraquinone prepared in Part C were treated with 4.02 g (26 mmole) of diethyl malonate and 9 mg of Na₂CO₃ for two hours at 180°-190° C. Volatiles were removed with an argon stream. After cooling, the product was filtered and the residue was washed with alcohol, hot water, and alcohol again and stirred overnight with 100 ml of toluene. After filtration and drying, the yield was 0.70 g (85%) of solid, 3'-carbethoxy-2-methyl-4-bromo-1,9-anthrapyridone, i.e.

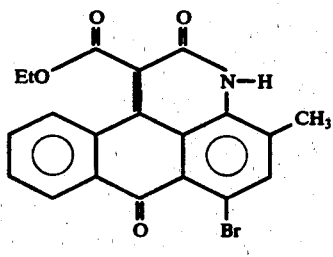

This material was not substantially soluble in water. Its solubility was estimated to be less than 50 ppm (basis water).

E. Preparation of a Supported Copper Material to be Used as a Coupling Catalyst

A 330 g portion of cupric acetic monohydrate was placed in a 50 l flask with 27 l of water and heated to 90° C. 3 kg of 28.3% concentration NH₄OH was added followed by 450 g of Aldrich dextrose and 300 g of Baker No. 345 Norite⁴ brand activated carbon in about 3 l of water. The black mixture was refluxed while 300 g of NaOH in 3 liters of water was gradually added over an hour period. The black solid which resulted was copper/copper oxide on carbon. It was isolated from the slurry by filtration and resuspended and filtered 3 times to yield about 700 g of final solid product.

F. Preparation of a Nonsolubilized Polymeric Colorant

A 100 ml, one-necked flask was charged with 0.32 g (4 mmole) of the poly(vinylamine hydrochloride) prepared in Example I, 1.70 g (16 mmole) of Na₂CO₃ and 16 ml of H₂O. The mixture was stirred until a homogeneous solution was obtained and 32 ml of ethylene glycol was added. Then 0.82 g (2 mmole) of 3'-carbethoxy-2-methyl-4-bromoanthrapyridone prepared in Step D was added to the mixture along with 0.4 g of the copper/copper oxide on carbon catalyst prepared in Step E. The entire mixture was placed in an oil bath preheated to 110° C and stirred vigorously. The disappearance of the bromoanthrapyridone was followed by TLC using ethylacetate elution. The reaction was over in 15-20 minutes.

The reaction mixture was filtered to removed solid residues. A clear solution of the red polymeric dye in 2:1 ethylene

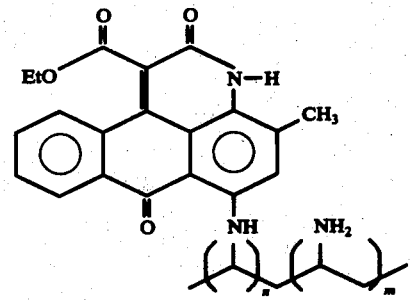

glycol/water was obtained. This polymeric dye was not soluble in water to an extent to permit its use in most desired aqueous applications. n and m were calculated as being equal, i.e., $n = m$ based on feed radios. By analysis, n was seen to equal 0.95 m.

G. Attachment of Solubilizing Groups

The glycol/water solution of Step F (pH 10.5) was treated with 5.56 g (40 mmole) of trimethylamine-sulfur trioxide complex for 48 hours at room temperature. The pH was maintained at 10-11 by the addition of 2.5N NaOH as necessary. The reaction mixture was then heated to 50° C for 4 hours (pH maintained at 10.5). After cooling, the mixture was filtered to remove solid impurities and the filtrate was extracted with ethylacetate until the product was essentially free of monomer by thin layer chromatography. The product solution was then dialysed against dilute saline through cellulose acetate, filtered through a Millipore⁴ microfilter, and freeze-dried. The yield of product was 0.42 g.

The final red dye (dye VII) had a λ max of 517 nm with ε = 12.9 A drop of an aqueous solution of the dye dissolved in 0.05N HCl with no haze. The final dye has solubility in water to at least 3000 ppm weight, basis weight. The final dye was determined to have a structure wherein $n = 0.95\ m$ and $n + m = 350$; and a molecular weight of about 100,000 based upon gel permeation chromatography comparison with polystyrene sulfonate standards of known size.

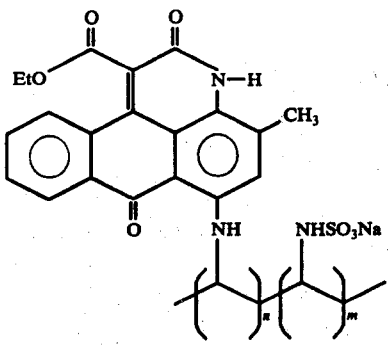

EXAMPLE VIII

Preparation of a red colorant:

A. Coupling of Chromophores

To a solution of 1.87 g (1 equivalent) of the poly(N-methylvinylamine hydrochloride) prepared in Example II, in aqueous ethylene glycol (2:1 glycol/water) containing 4 equivalents of $Na_2CO_3$ was added one-half an equivalent of the 3′-carbethoxy-2-methyl-4-bromo-1,9-anthrapyridone prepared in step D of Example VII and 2.0 g of the copper catalyst prepared in Step E of Example VII. The reaction required 1.5–2.0 hours to go to completion at 110° C. The catalyst and other solid contaminants were removed by filtration to yield a solution of the not substantially water soluble coupled colorant

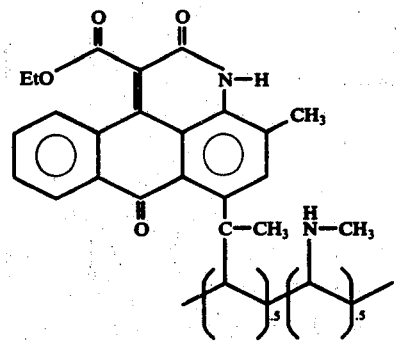

B. Solubilizing of the colorant product

To the aqueous ethylene glycol solution of polymeric colorant prepared in Step A was added a 15-fold excess of trimethylamine-sulfur trioxide complex. The mixture was held at pH 10.5– 11.0 for 24 hours at 25° C and for 2 hours at 45° C. The resulting soluble polymeric dyes was isolated in a yield of 1.51 g by ethyl acetate extraction, dialysis against dilute saline through cellulose acetate and freeze drying. The dye, Dye VIII, had the structure:

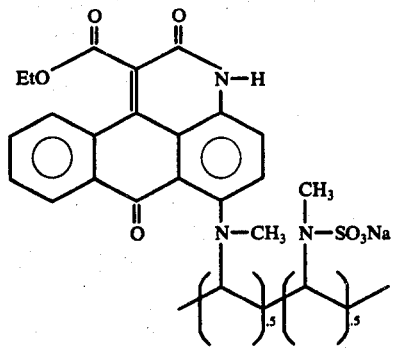

EXAMPLE IX

A. Preparation of 3′-acetyl-2-methyl-4-bromo-1,9-anthrapyridone

A 100 ml flask was charged with 3.6 g (10 mmole) of the 1-amino-2-methyl-4-bromoanthraquinone of Part C of Example VII, 10 ml (10.2 g, 78.5 mmole) of ethyl acetoacetate and 0.033 g (0.31 mmole) of sodium carbonate. The mixture was heated under a slow argon flow in a 180°-190° C oil bath with stirring. Lower boiling materials ($H_2O$, EtOH, etc.) were distilled off as they were produced. After heating for 1.5 hours, a thin layer chromotogram (silica gel, ethyl acetate) of the reaction mixture was cooled and filtered. The residue was washed with ethanol, hot water, and ethanol, then the residue was stirred with boiling toluene for 5 mintues and filtered. This process was repeated four times an the final residue was dried in a 44° C vacuum oven overnight to yield 3.32 g (87% yield) of 3′-acetyl-2-methyl-4-bromo-1,9-anthrapyridone, i.e.,

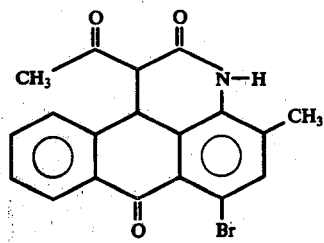

B. Coupling of Dye Chromophore to a Polymer

A 100 ml. one-necked flask equipped with a magnetic stirring bar was charged with 0.16 g (2.0 mmole, 1 equivalent) of the poly(vinylamine hydrochloride) of Example I, 0.85 g (8 mmole, 4 equivalents) of $Na_2CO_3$ and 8 ml of $H_2O$. The mixture was stirred until a homogeneous solution was obtained at which point 16 ml of ethylene glycol was added. The solution remained homogeneous and the pH was 10.5–11.0. Then, 0.66 g (1.7 mmole, 0.85 equivalent) of 3′-acetyl-2-methyl-4-bromoanthrapyridone prepared in Step A of this Example was added to the mixture along with 0.20 g of a Cu-CuO-C catalyst prepared in accord with Example VII. The entire mixture was placed in an oil bath preheated to 110° C and stirred vigorously. The disappearance of the bromoanthrapyridone was followed by thin layer chromatography (silica gel, ethyl acetate elution) and was complete after 1/2 hour. The reaction mixture was cooled and filtered to remove catalyst and other solid contaminants leaving a bright red solution of polymeric dye.

C. Solubilization

The red dye solution (2 mmole) was treated with 12.51 g (90 mmole) of sulfur trioxide-trimethylamine complex at a pH between 10.0–11.0 (maintained by adding 2.5 N NaOH when necessary). The sulfur trioxide complex was added in three equal portions. The first portion was added to 0° C for ½ hour and at room temperature for 12 hours. The second portion was added at room temperature followed by heating at 70° C for 4 hours. Then, the mixture was cooled and the third portion was added and the mixture was heated at 45° C and stirred for 36 hours.

The reaction mixture was cooled and filtered to remove the excess undissolved complex. The reaction mixture was diluted to 250 ml and extracted with ethyl acetate (8 times, 1.5 l total). After extraction, the clear red solution was dialysed vs. 0.5% NaCl solution, passed through an 8μ milliporous microfilter and freeze dried. 0.51 g of final dye was recovered having the formula

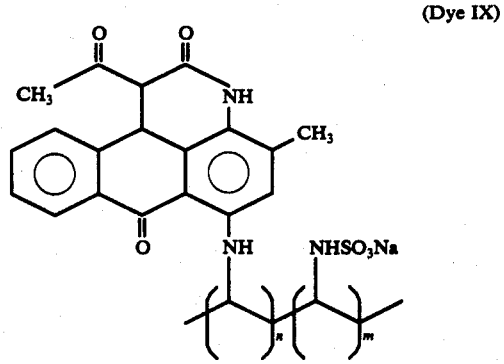

(Dye IX)

(wherein $n = 0.70$ and $m = 0.30$ and calculated molecular weight of 140,000). This produce was water-soluble, while the nonsulfonated product was not suitably soluble in water. Its color properties include a λ max of 520 nm and ε of 11.9.

EXAMPLE X

A. Preparation of N-Acetyl-1-Methylamino-4-Bromoanthraquinone

A 250 ml flask equipped with a mechanical stirred was charged with 30 g (95 mmole) of 1-methylamino-4-bromoanthraquinone (purchased from Sandoz), 19.5 g (191 mmole) of acetic anhydride, and 0.23 g of 96% $H_2SO_4$. The sludgelike mixture was heated and stirred at 110° for 30 minutes. The reaction mixture was cooled to 0° and 50 ml of $H_2O$ was added. After stirring ½ hour, 55 ml of 30% NaOH was added and the entire mixture was then transferred to a pressure reactor for the following reaction. A TLC (EtOAc) showed only a single product in the reaction.

B. Preparation of 1'-Methyl-4-Bromoanthrapyridone

The acetyl anthraquinone from Part A was placed in a pressure vessel and heated and stirred at 120° for 2 hours. The reaction mixture was cooled, filtered, and washed with $H_2O$. After oven drying, the brown solid was dissolved in 200 g of 96% $H_2SO_4$ and reprecipitated by the addition of 40 ml of $H_2O$. The solid was filtered and washed with 25 g of 78% $H_2SO_4$. The filter cube was then stirred with 800 ml of $H_2O$, filtered, washed, and dried in vacuo. The solid then obtained was twice recrystallized from trichloroethane to afford 8.5 g of pure anthrapyridone.

C. Polymer Attachment Step

A 250 ml round bottomed flask was charged with 480 mg (6.0 mmole) of poly(vinylamine) of Example I, 2.54 g (24.0 mmole) of $Na_2CO_3$, and 36 ml of $H_2O$. The mixture was stirred until solution was complete and 72 ml of ethylene glycol was added. Then, 510 mg (1.50 mmole, 0.25 equivalents) of 1'-methyl-4-bromoanthrapyridone was added along with 50 mg of $Cu_2O$. The reaction mixture was then placed in a pre-heated oil bath, refluxed for ten minutes, and rapidly filtered. The red polymeric dye obtained in the filtrate is of the following composition.

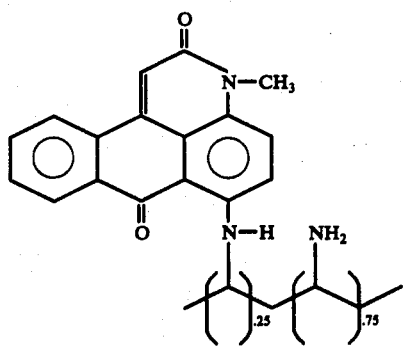

D. Water Solubilization Step

The filtrate of Step C was treated with 5.56 g of trimethylaminesulfurtrioxide with stirring for 17 hours at room temperature. The crude product was then filtered to remove insolubles, extracted with EtOAc, and dialysed vs. dilute saline solution through a cellulose acetate membrane. The product was isolated in 49% yield after freeze drying. The composition of the product (Dye X) was:

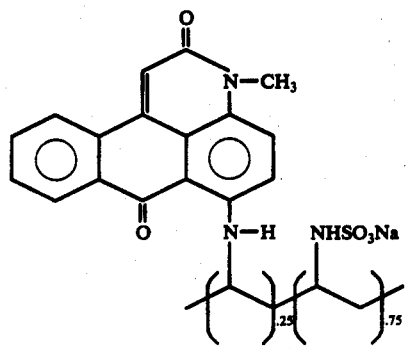

EXAMPLE XI

Preparation of a water-soluble blue polymeric dye:

A. Coupling of Dye to Polymer

Poly(vinylamine hydrochloride) (0.76 g, 9.56 mmole) prepared in Example I was placed in a 100 ml flask. Five ml of water was added to dissolve the amine. Then 25 ml of ethylene glycol was added followed by concentrated NaOH to pH 9.2. Cu/CuO on carbon catalyst, (1.15 g) prepared in Example VII, Step E and 1.86g(5.89 mmole) of 1-N-methylamine-4-bromoanthraquinone,

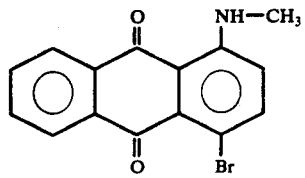

obtained from Benzenoid Organics, were added along with about 5 ml of additional ethylene glycol.

The flask was heated to 110°–120° C for 60 minutes followed by pH adjustment with NaOH to pH 10.5–11.0 and refluxing at 125° C for 2½ hours. This resulted in the formation of a solution of the polymeric blue colorant which was filtered to remove solids.

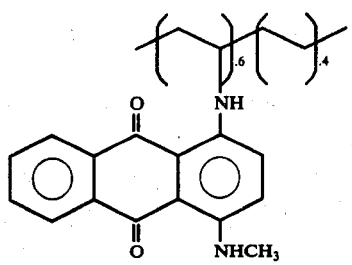

B. Solubilization

The solution prepared in Step A was diluted with 10 ml of water. A substantial excess over stoichiometric or trimethylamine - SO₃ complex was added followed by 5 ml of ethanol. The mixture was stirred overnight. The reaction mixture was then "ultrafiltered" with an Amicon Corp. ultrafiltration membrane having a 10,000 MW cut off. The retentate was treated with NaOH, filtered to remove solids, extracted with ether and freeze dried to yield the solid water-soluble blue colorant (Dye XI).

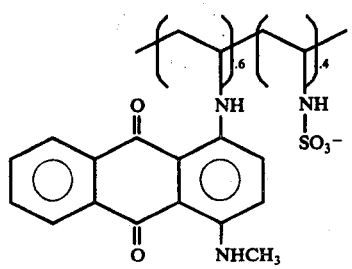

EXAMPLE XII

Preparation of a purple polymeric colorant:

A. Preparation of Chromophore
Benzathrone,

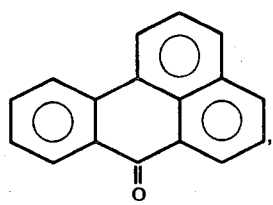

was vacuum sublimed. A 12.1 g portion (52.7 mmoles) was placed in a flask and dissolved in 50 ml of acetic acid with warming. 9.3 g of neat bromine was added along with 65 ml of additional acetic acid and 30 ml of nitrobenzene. The mixture was stirred and gradually heated — finally being maintained at 90° C for 12 hours. The reaction mixture had become homogeneously yellow. The mixture was cooled and poured into a liter of water and 500 ml of dichloromethane to yield two phases. The color went to the organic phase which was isolated, dried with Na₂SO₄, filtered and evaporated to yield a solid purple chromophore which upon analysis was found to be:

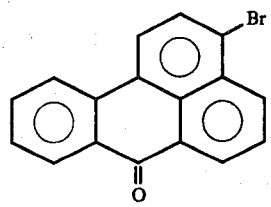

B. Coupling 385 mg (3.81 mmole, 1 equivalent) of the poly(N-methylvinylamine hydrochloride) of Example II and 10 ml of water and 25 ml of ethylene glycol are placed in a 100 ml flask. 1.62 g (15.2 mmole) of sodium carbonate, 1.0 g (3.24 mmole, 0.85 equivalents) of the chromophore of Part A, and 50 mg of a cupric acetate catalyst are added and the mixture is heated to 110° C and there maintained for 2–3 hours. Solids are removed by filtration to yield a clear ethylene glycol/water solution of the purple colorant

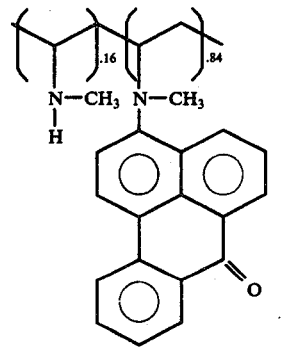

This material is not substantially water-soluble.

C. Solubilization

To solution of Part B is added a substantial excess of triethylamine-SO₃ complex (15 equivalents based on original amine content). The mixture is stirred at 40° C for 12 hours. The resulting solution of soluble polymeric dye is purified by millipore filtration to remove solids and dialysis through cellulose acetate against dilute saline solution to remove salts and then freeze dried to isolate the purple solid which is shown to be (Dye XII)

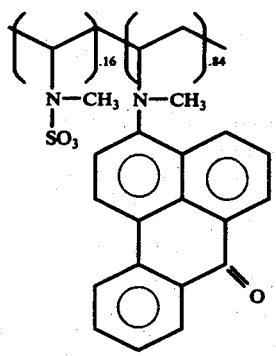

and to have a molecular weight of about 55,000, as calculated from the weight of the starting poly(amine).

EXAMPLE XIII

Preparation of a polymeric yellow colorant:

A. Preparation of Chromophore

Using the general method disclosed in Patki et al, Indian Journal of Technology, Vol. 12 (1974) p 540-545, 31.6 g (100 mmole) of the anthraquinone product of Example VII, Step C, is suspended in 100 ml of water. Sodium hydroxide (15 g in 60 ml of water) is added with stirring followed by 70 g (1.2 mole) of acetone. The mixture is refluxed for 20 hours. A TLC test indicates that the anthraquinone and acetone have reacted to completion. The mixture is cooled, neutralized with hydrochloric acid, and filtered to recover the yellow precipitate of 2,4-dimethyl-6-bromopyridinanthrone

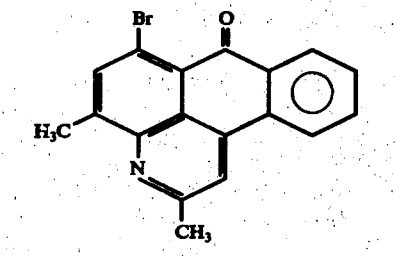

which is washed with water and dried.

B. Coupling

A 100 ml flask is charged with 0.64 g (8 mmole) of the poly (vinylamine hydrochloride) of Example III, 3.4 g (32 mmole) of $Na_2CO_3$, 32 ml of water followed by 65 ml of ethylene glycol. Then 1.69 g (5.0 mmole) of the product of Step A, along with a catalyst consisting of 0.25 g of finely powdered cuprous oxide is added and the mixture is stirred at 100°-110° C for 30 minutes. The reaction mixture is filtered to remove solids and yield a yellow glycol/water solution of the polymeric colorant:

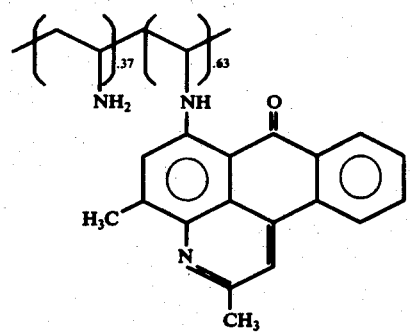

This material is not substantially soluble in water.

C. Solubilization

The solution prepared in Step B is subjected to solubilization.

The solution is maintained at pH 10.5-11.0 by base addition while 8.34 g (60 mmole) of trimethylamine-sulfur trioxide complex are added. The mixture is heated to 50° C for 5 hours, cooled and filtered to remove solid. The filtrate is extracted with ethyl acetate, dialyzed against saline with a cellulose acetate membrane, and freeze dried to yield as a water-soluble final colorant product (Dye XIII).

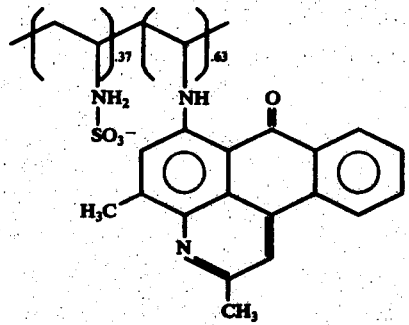

EXAMPLE XIV

The preparation of Example XIII is repeated with one modification. Instead of 1-amino-2-methyl-4-bromoanthraquinone, 1-amino-4-chloroanthraquinone (prepared by reacting 1-benzamido-4-chloroanthraquinone with concentrated $H_2SO_4$ at 95°-100° C) is used as starting material.

EXAMPLE XV

A. Chromophore preparation 1-amine-4-bromoanthraquinone, acetoacetic acid ethyl ester and alkane sulfonic acid catalyst are reacted in accordance with the teachings of Example 1 of U.S. Pat. No. 2,759,940 issued Aug. 21, 1956 to Bucheler et al., (which patent is herein expressly incorporated by reference) to yield the yellow chromophore

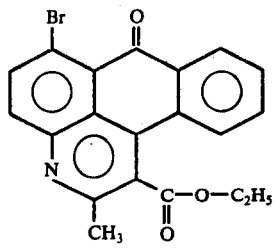

B. Coupling of Chromophores to Backbone 0.37 g (4 mmole) of the poly(isopropenylamine) hydrochloride prepared in Example V is dissolved in 48 ml of 2:1 ethylene glycol/water along with 1.70 g of $Na_2CO_3$. Then, 0.79 g (2 mmole) of the chromophore of Step A is added along with 0.3 g of cupric acetate monohydrate catalyst. The mixture is heated at 100° C for 40 minutes.

The reaction mixture is filtered to remove solid residues and yield a solution of the yellow polymeric colorant

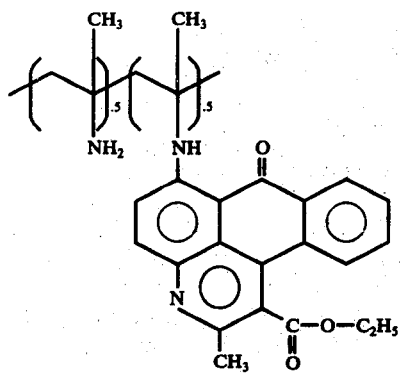

C. Solubilization

The solution of yellow colorant of Step B is treated with trimethylamine sulfurtrioxide complex in accord with the procedure of Example VIII, Step G to produce the sulfamated soluble product yellow colorant (Dye XV):

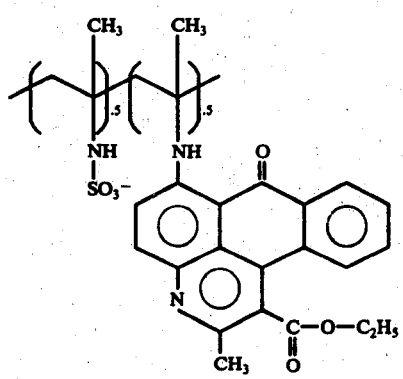

which product is isolated as a freeze-dried solid.

EXAMPLE XVI

Following the teachings of Example IX of herein-incorporated U.S. Pat. No. 2,759,940, the yellow chromophore

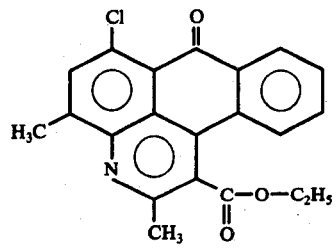

is prepared. This material (0.8 mmoles) is coupled to the poly(vinylamine) of present Example I (1.0 mmoles) using the procedure of Step F of Example VII and the resulting product is solubilized and recovered in accord with the procedures of Step G of Example VII to yield as a final water-soluble yellow colorant (Dye XVI):

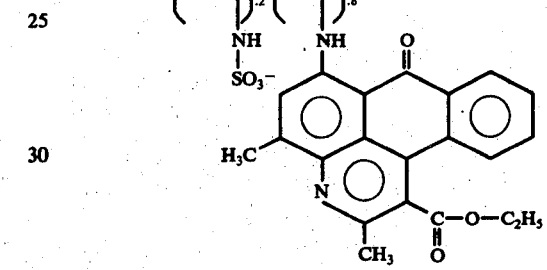

EXAMPLE XVII

A. Coupling of Chromophore to Backbone

Poly(vinylamine hydrochloride) (0.24 g, 3 mmole) prepared in Example I is dissolved in 12 ml of water in a 100 ml flask. 1.27 g of sodium carbonate (12 mmole) is added followed by 24 ml of ethylene glycol, 0.51 g (1.5 mmole) of monomeric chromophore

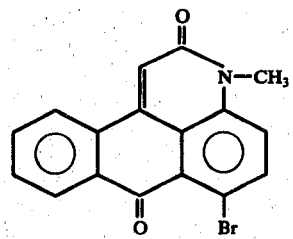

prepared in Example X, Step B, and 0.3 g of the Cu-CuO-Carbon catalyst prepared in Example VII, Part E, are added and the mixture is reacted for 30 minutes at 110°-115° C. The reaction mixture is cooled to 40°-60° C, filtered through sintered glass and diluted to 100 ml with rinse glycol and excess water. This addition of water causes the colorant to form a suspension. The red polymeric colorant suspended in the glycol/water mixture has the formula:

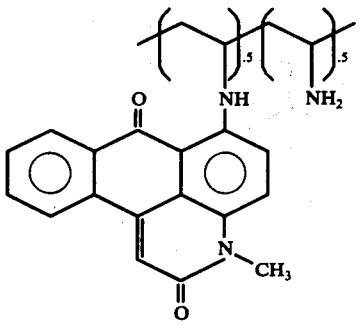

B. Solubilization

A 30 ml portion of the suspension prepared in Step A was placed in a 200 ml beaker. The pH of the suspension was adjusted to 9.5. Over a 9 hour period, 1.069 g of propane sultone was gradually added. After seven hours, the pH dropped to 10.5. At the completion of propane sultone addition, the suspension had become a homogeneous solution.

About 20 ml of NH₄OH (Baker 28%) was added to destroy unreacted propane sultone. The mixture was stirred for ¼ hour and the pH of the mixture was brought to 9.6 by addition of 4N hydrochloric acid. 20 g of sodium chloride was added which caused the polymer to begin to "salt out." The resulting slurry was dialyzed overnight against water. As the salts and glycol diffused out, the precipitates went back into solution. The solution was filtered with a Millipore$^R$ filter to remove solids and the filtrate was lyophilized to yield 0.136 g of the red polymeric dye (Dye XVII):

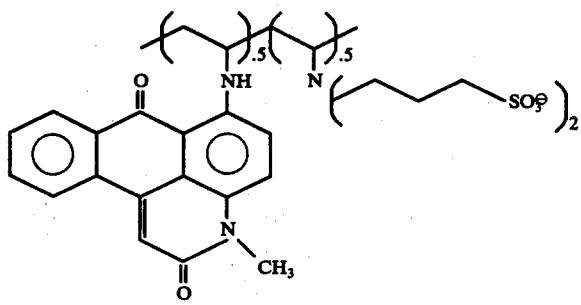

This product gave clear red 1000 ppm solutions in water at pH's 2 through 12.

EXAMPLE XVIII

A 30 ml portion of the suspension prepared in Step A of Example XVII is placed in a 200 ml beaker. The pH of the suspension is adjusted to pH 9.5. Over a 9 hour period 1.19 g of butane sultone is added. At the completion of butane sultone addition, a homogeneous solution has resulted.

Unreacted sultone is consumed by NH₄OH addition and then the pH is brought to about 9.5 by hydrochloric acid addition. The solution is dialyzed to remove salts and glycol, is filtered to remove solids, and is lyophilized to yield the red polymeric dye (Dye XVIII):

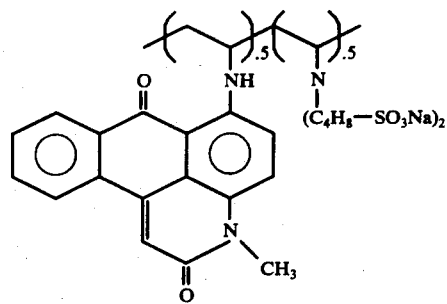

EXAMPLE XIX

A. Preparation of Solubilizing Agent

Carbly sulfate

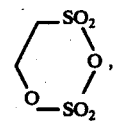

is prepared following the method disclosed by D. S. Breslow and R. R. Hough in their article appearing at page 5000 of Volume 79 of the *Journal of the American Chemical Society* (1957) wherein ethylene is reacted with two equivalents of sulfur trioxide in vapor phase at 150°-165° C. This article is expressly incorporated herein by reference.

B. Solubilization of a Polymeric Dye

Following the general method described in Farbwerke Hoechst's Belgian Patent 620,445 dated Jan. 21, 1963, abandoned which patent is herein incorporated by reference, 0.812 g of water-insoluble polymeric red colorant of the formula

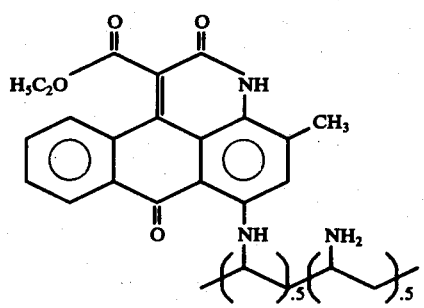

having 1 mmole of primary amine groups, having a molecular weight of about 85,000 and prepared in accordance with the method of Example VII, Step F, is added to 10 ml of water, 20 ml of ethylene glycol and 0.138 g (1 mmole) of potassium carbonate. 0.38 g (2 mmole) of carbyl sulfate, prepared in Step A of this Example is then added at 0°-5° C over 20 minutes with stirring. The pH is maintained at 10-11 by addition of aqueous KOH. A solution of the water-solubilized dye of the formula (Dye XIX):

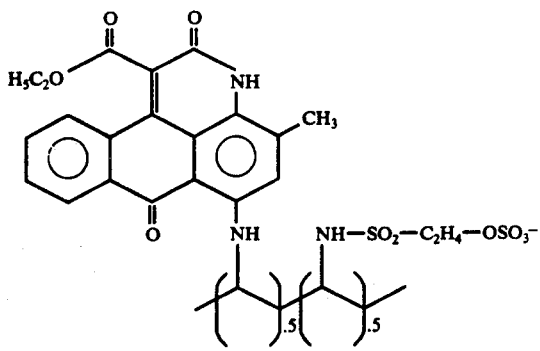

results with is neutralized, filtered to remove solids, diaylzed to remove salts and spray-dried.

EXAMPLE XX

A. Preparation of Chromophore 4.4 g (10 mmole) of D&C Orange No. 4,

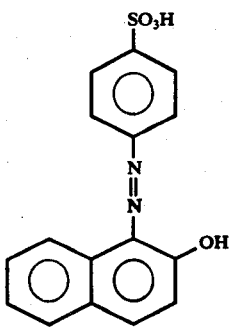

is reacted overnight at room temperature with an excess of acetic anhydride in pyridine to acetylate the naphthyl hydroxyl group. The acetylated product is recoverd, and added to a solution of one equivalent thionyl chloride in 100 ml of benzene containing a catalytic amount of DMF. After stirring for 2 hours at room temperature, the bright orange chlorosulfonate derivative,

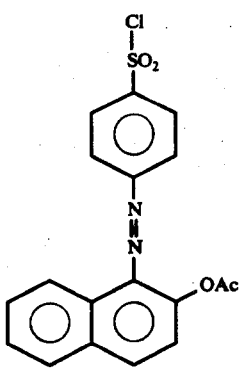

is recovered.

B. Coupling of Chromophore to Backbone 7.0 g of the poly(vinylamine hydrochloride) prepared in Example I is added to a 2000 ml flask, 700 ml of water and 350 ml of tetrahydrofuran are added and the pH is raised from 2.5 to 9.5 by addition of 2.5 N NaOH.

Next 13.7 g (0.4 equivalents, based on total amine polymer) of the chromophore of Part A is slowly added at room temperature while maintaining the pH at 9.0–9.5 by NaOH addition. Additional THF and NaOH are added and the pH is raised to 9.5–10.5. The product,

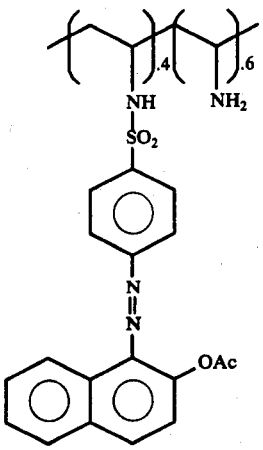

is not isolated, but is used immediately for Step C.

C. Solubilization

The product of Step B at a pH of 10.5 is treated with an excess of trimethylamine-sulfurtrioxide complex for 24 hours at room temperature and at 50° C for 4 hours. The pH is maintained at 10.5 by adding NaOH. This causes the primary amine groups on the backbone to be sulfamated and the chromophore acetate groups to hydrolyze. The resulting product is neutralized to yield a solution of the polymer (Dye XX):

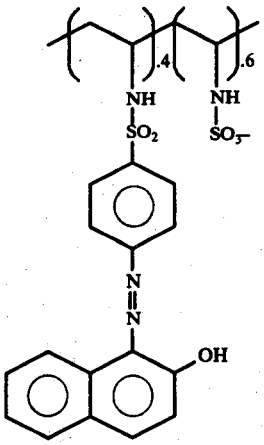

The solution is filtered, dialyzed and lyophilized to yield the product as a solid.

EXAMPLE XXI

A. Preparation of Chromophore

Following the general teachings of R. C. Fuson and C. H. McKeever at pages 70–71 of Volume I of *Organic Reactions* (Wiley and Sons, Inc., 1942) D and C Orange No. 4 is contacted with 35% formalin and concentrated hydrochloric acid at 10° C for 3 hours. The reaction mixture is neutralized with NaOH, dialyzed to remove salts, and unreacted formaldehyde and the chloromethylated reaction product,

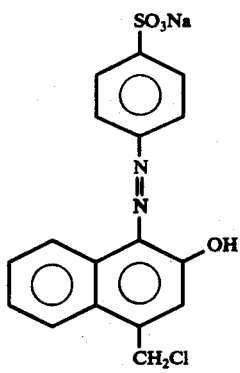

is isolated.

B. Coupling 1.0 equivalents of the poly(isopropenylamine) hydrochloride prepared in Example V are dissolved in water. 1.0 equivalents of NaOH are then dissolved followed by 0.5 equivalents of the chromophore of Step A. The mixture is stirred at 50° C overnight, thereby causing the chromophore to displace amine hydrogens on the backbone and form:

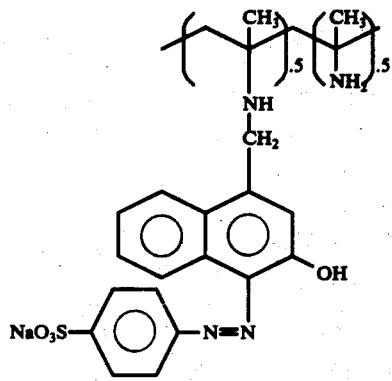

This product is precipitated and recovered by adjusting the pH to 7.5–8.0:

C. Solubilization

The product of Step B is relatively soluble at pH's greater than 9.5. Complete water solubility imparted to it by adding a 10-fold excess of trimethylamine-sulfurtrioxide complex to a solution of the product and stirring the mixture at 25° C for 24 hours at pH 10.5–11.0. This results in the formation of the product (Dye XXI),

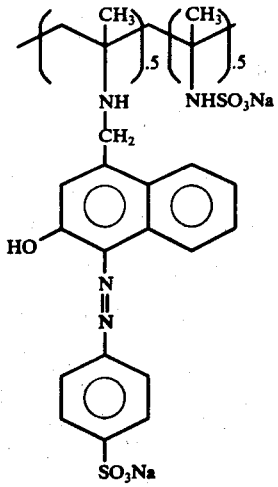

which product is recovered by freeze drying after dialysis to remove salts and microfiltration to remove undesired solids.

EXAMPLE XXII

A. Polymer Attachment 268 mg (2 mmoles) of poly(dialkylamine HCl) was placed in a 50 ml, 100 ml bottom and dissolved in 5 ml of $H_2O$. Then, 425 mg (4 mmoles) of $Na_2CO_3$ and 10 ml of ethyleneglycol was added. After stirring until a completely homogeneous mixture was obtained, 412 mg (1 mmole) of 3'-carbethoxy-2-methyl-4-bromoanthrapyridone (Example VIII, Step D) was added along with 200 mg of powdered $Cu_2O$. The mixture was then vigorously refluxed for ½ hour and filtered at the boil through a medium sintered glass funnel. The aqueous filtrate contained bluish red dye of the following composition:

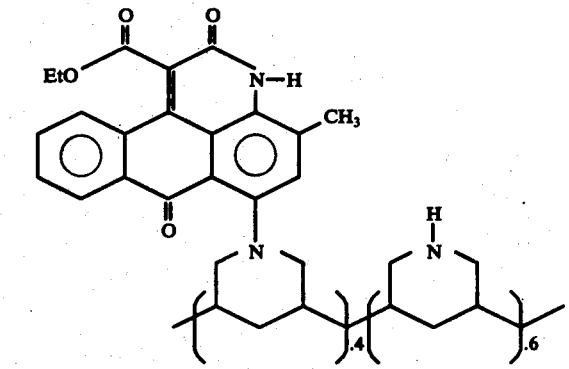

B. Water Solubilization Step

The reaction mixture from Step A was diluted with 50 ml of $H_2O$ and stirred for 24 hours at room temperature with 3.0 g of trimethylamine-sulfur trioxide at pH 10.5–11.5. The reaction mixture was heated for two hours at 50°, filtered, and exhaustively extracted with ethyl acetate. The dye solution was then dialyzed through cellulose acetate vs. dilute EDTA at pH 9.5 for 3 days. This was followed by dialysis against dilute NaCl solution for 24 hours and finally dialysis against pure $H_2O$ for 12 hours. The final solution was filtered through a micropore filter and freeze dried to afford 244 mg of a red polydye with the following composition:

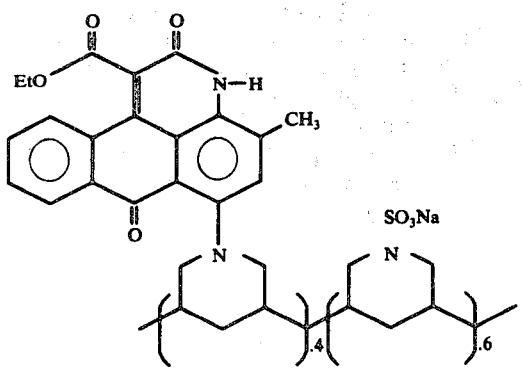

EXAMPLE XXIII

A. Preparation of Chromophore 1. 3'-Carbethoxy-2-Bromo-4-p-Toluidinoanthrapyridone 31.4 g (77.1 mmoles) of 1-amino-2-bromo-4-p-toluidinoanthraquinone (Benzenoid Organics Inc.), 250 ml of diethylmalonate, and 0.63 g of sodium acetate were heated at 180°–185° under an argon stream for 105 minutes. During this period the reaction mixture turned from deep blue to purplish red. The reaction mixture was cooled to 45° and the excess diethylmalonate was removed in vacuo (0.25 mm). The product was dried at 80°/0.1 mm for 18 hours and had the following structure:

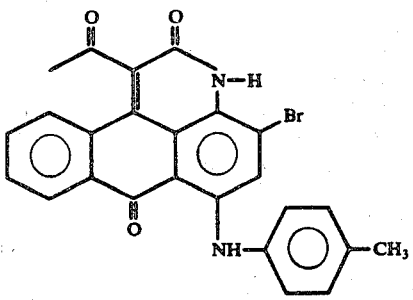

2. Potassium 3'carbethoxy 4-p-Toluidinoanthrapyridone-2-Sulfonate

The crude product from the above reaction (38.8 g, 77.1 mmoles) was refluxed with 40.0 g of $K_2SO_3$ in $H_2O/\phi$-OH (3:7). The course of the reaction was followed by TLC (5% MeOH/CHCl$_3$ elution on silica gel). After 48 hours, the reaction was judged complete. The phenol was removed with steam, at which point the product precipitated. The royal purple product was filtered and dried in vacuo to afford 39.7 g of monomeric dye of the following structure:

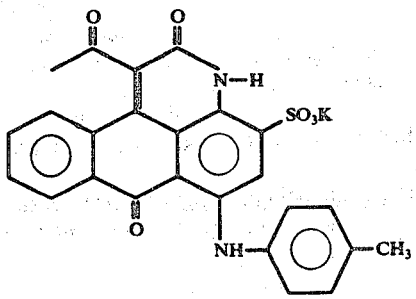

3. 3'-Carbethoxy-4-p-Toluidinoanthrapyridone-2-sulfonyl Chloride 3.90 g (7.2 mmole) of the above anthrapyridone sulfonate, 83.5 g (0.71 mole) of thionyl chloride, and 25 drops of DMF were stirred at room temperature for 7 days in 100 ml of 1,1,2,2-tetrachloroethane. The excess reagent and solvent were removed by vacuum distillation and the purple residue was dissolved in methylene chloride and filtered to remove KCl. Removal of the solvent and drying in vacuo afforded a quantitative yield (3.76 g) of sulfonyl chloride.

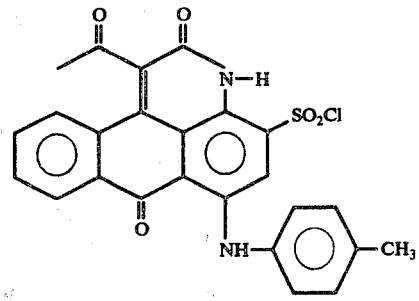

B. Chromophore Attachment (Schotte-Bauman Reaction)

318 mg (4.0 mmoles) of poly(vinylamine) hydrochloride (prepared in Example I) was dissolved in 15 ml of $H_2O$ and the pH was raised to 10.0 by the addition of 10% NaOH solution. To To the solution was added 349 mg (0.66 mmole) of the anthrapyridone sulfonyl chloride of Part A and 5 ml of ethylene glycol. These additions were repeated twice more over a period of 7.5 hours as the pH was maintained at 9.5–10.5 by the addition of NaOH as necessary.

The product of this reaction was not isolated, but was subjected immediately to solubilization.

C. Solubilization

The reaction mixture of Part B was diluted to 100 ml with water and treated with 20 equivalents (5.56 g, 40.0 mmoles) of trimethylamine sulfur trioxide at room temperature for 36 hours. The pH was maintained at 10.5–11.5 by the addition of 2.5 N NaOH solution as necessary. The reaction mixture was neutralized (2 N HCl) and dialyzed in a cellulose acetate bag for 48 hours in a bath consisting of 33% aqueous pyridine containing 0.5% by weight $Na_2SO_4$. Following this, dialyses were carried out against 0.5% $NaHCO_2$ in water (24 hours), 1% NaCl in water (24 hour), and finally pure water (24 hours). The royal purple solution was filtered (micropore membrane) and freeze dried to afford 853 mg of product. Gel permeation chromatography using sulfonated polystyrene standards indicated the molecular weight of the product was 105,000. Elemental analysis showed the product to be of the following structure:

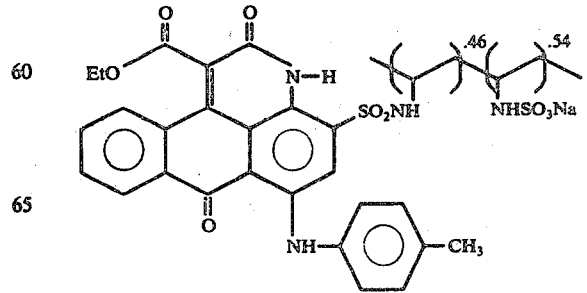

The dye had a λ max of 544 nm with ε 9.2.

EXAMPLE XXIV

A. Preparation of Chromophore 1. 3'-Carbethoxy-2-methyl-4-anilinoanthrapyridone 4.12 g (10 mmole) of 3'-carbethoxy-2-methyl-4-bromoanthrapyridone (purchased from Sandoz Colors and Chemicals) was stirred under an inert atmosphere with 25 ml of aniline in a bath maintained at 145°–150°. After 2.5 hrs, TLC (EtOAc on silica gel) indicated the complete disappearance of starting material with the formation of a sole product. Removal of the excess aniline by vacuum distillation followed by drying in vacuo (100°/0.1 mm) afforded a quantitative yield of product (4.24 g).

2. Chlorosulfonation 4.00 g (9.43 mmole) of 3'-carbethoxy-2-methyl-4-anilinoanthrapyridone was dispersed in 25 ml of $CHCl_3$ and the mixture was cooled to 0°. To the mixture was added dropwise over a period of 1 hr 5 equivalents (4.10 g) of chlorosulfonic acid. After stirring at 0° for an additional 1 hr, the reaction mixture was filtered and the product was washed well with $CHCl_3$ (0°) and then dried in vacuo to afford 4.66 g (8.91 mmoles) of sulfonyl chloride as a violet-red cyrstalline solid. Elemental analysis confirms the following structure:

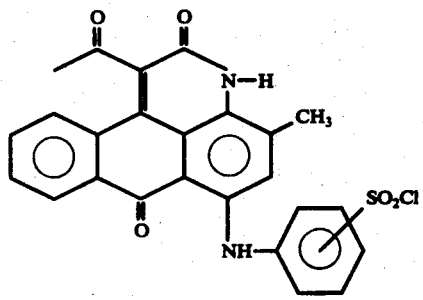

B. Coupling 523 mg (1.0 mmole) of the above sulfonyl chloride was treated with 3.0 mmoles (238.5 mmoles) of poly(-vinylamine) in 40 ml of THF-$H_2O$ (1:3) at room temperature and pH 10.5–11.0. This afforded a red polymeric dye with poor water solubility of the following structure:

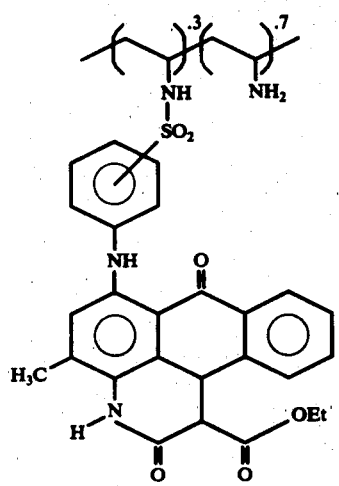

C. Solubilization

The crude dye solution, after the addition of 100 ml of water, was treated with 5.56 g (40 mmoles) of trimethylamine-sulfur trioxide at room temperature and pH 10.5–11.0 for 36 hours. Purification was carried out as described in Example XXIII, Section C to afford 689 mg of bluish red polydye of λ max 510 with ε 7.8. Gel permeation chromotography showed the molecular weight of the product was approximately 98,000. Elemental analysis agreed with the following structure:

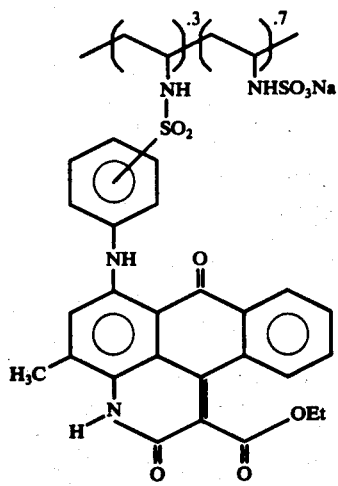

EXAMPLE XXV

The colorants of the present invention prepared in the foregoing Examples are employed as food colors.

100 ppm by weight of the red colorant of Example VII is added to an uncolored soft drink so as to form a "cherry soda" appearing beverage.

50 ppm by weight of the red colorant of Example VIII is dissolved in a sweetened and flavored gelatin solution, the solution is set to yield a "cherry" or "strawberry" gelatin dessert.

200 ppm by weight of the red colorant of Example IX is dissolved in cough syrup to make its appearance more pleasing and "cherry-like."

The yellow colorant of Example XIII is added to a prepared white cake mix at a use level of 150 ppm along with lemon flavor. The mix is baked yielding a "lemon" yellow style cake.

What is claimed is:

1. A water-soluble polymeric coloring composition consisting essentially of $n$ units of an organic optically chromophoric group, A, and $m$ units of a sulfur oxide water-solubilizing groups selected from the group consisting of sulfonate group and 2 to 4 carbon alkyl sulfonate groups attached through amine linkages selected from the group consisting of the secondary amine linkage and 1 to 4 carbon alkyl-substituted tertiary amine linkages directly to separate carbon atoms of a saturated aliphatic hydrocarbon backbone, wherein $n$ is from 0.2 to 4 times $m$, the sum of $n$ plus $m$ is a value from 20 to 3000 and the coloring composition has a molecular weight of from 2000 to 2,000,000.

2. The water-soluble polymeric coloring composition of claim 1 wherein said amine linkages are secondary amine linkages.

3. The water-soluble polymeric coloring composition of claim 1 wherein the organic optically chromophoric group comprises an optically chromophoric anthraquinone group.

4. The water-soluble polymeric coloring composition of claim 1 wherein the sulfur oxide water-solubilizing group is sulfonate.

5. A water-soluble polymeric coloring composition consisting essentially of m

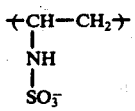

groups and

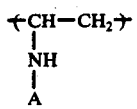

groups randomly linked together through covalent carbon-carbon bonds into a

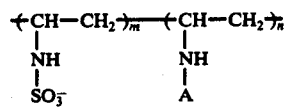

polymer having a linear aliphatic hydrocarbon backbone wherein n and m are integers such that the sum of n plus m is a value of from 20 to 3000, n is from 0.2 to 4 times m, A is an optically chromophoric organic group and the coloring composition has a molecular weight of from 2000 to 2,000,000.

6. The coloring composition of claim 5 wherein A is an optically chromophoric organic anthraquinone group.

7. A water soluble coloring composition comprising n

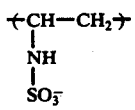

groups and m

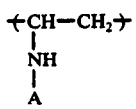

groups randomly linked together through covalent carbon-carbon bonds into a linear aliphatic polymer wherein n and m are integers such that the sum of n plus m is a value of from 20 to 3000, n is from 0.4 to 2 times m and A is an optically chromophoric group represented by the formula:

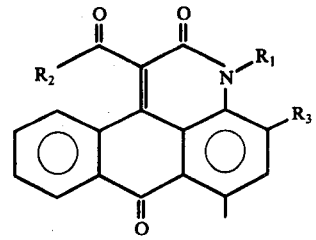

wherein $R_1$ is selected from the group consisting of hydrogen, lower alkyls of from 1 to 4 carbon atoms and aryls of about 6 carbon atoms, $R_2$ is selected from the group consisting of 1 to 4 carbon atom lower alkyls, 1 to 4 carbon atom lower alkoxies, and aryls of about 6 carbon atoms, and $R_3$ is selected from the group consisting of hydrogen and 1 to 4 carbon atom lower alkyls.

8. The coloring composition of claim 7 wherein $R_1$ is hydrogen and $R_3$ is a lower alkyl of from 1 to 4 carbon atoms inclusive.

9. The coloring composition claim 8 wherein $R_2$ is methyl.

10. The coloring composition of claim 9 wherein $R_3$ is methyl.

11. The coloring composition of claim 8 wherein $R_2$ is methoxy or ethoxy.

12. The coloring composition of claim 11 wherein $R_3$ is methyl and $R_2$ is ethoxy.

13. The coloring composition of claim 7 wherein $R_1$ is a lower alkyl of from 1 to 4 carbon atoms and $R_3$ is hydrogen.

14. The coloring composition of claim 13 wherein $R_1$ is methyl.

15. The coloring composition of claim 14 wherein $R_2$ is methoxy.

16. The coloring composition of claim 14 wherein $R_2$ is methyl.

17. A water-soluble coloring composition comprising n

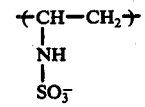

groups and m

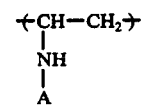

groups randomly linked together through covalent carbon-carbon bonds into a linear aliphatic polymer wherein n and m are integers such that the sum of n plus m is a value of from 20 to 3000, n is from 0.4 to 2 times n and A is an optically chromophoric group represented by the formula:

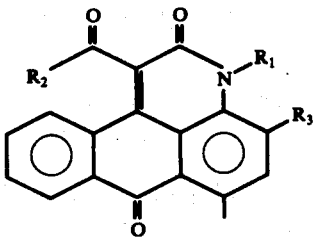

wherein $R_1$ is hydrogen or methyl, $R_2$ is selected from the group consisting of hydrogen and lower alkyls of from 1 to 4 carbon atoms and $R_3$ is selected from the group consisting of hydrogen, lower alkyls of from 1 to 4 carbon atoms, the halogens, cyano and nitro.

18. The coloring composition of claim 17 wherein $R_1$ is hydrogen and $R_2$ is methyl.

19. The coloring composition of claim 17 wherein $R_1$ is methyl, $R_2$ is hydrogen and $R_3$ is hydrogen.

20. A water-soluble coloring composition comprising $n$ optically chromophoric anthraquinone groups and $m$ sulfonate groups individually attached through amine linkages selected from the secondary amine linkage and 1 to 4 carbon alkyl-substituted tertiary amine linkages directly to essentially one-half the carbons of a linear aliphatic hydrocarbon polymer backbone of not less than 40 carbon atoms, wherein $n$ and $m$ are numbers and $n$ is from 0.2 to 4 times $m$ and wherein the composition is nontoxic, having a value for the sum of $n$ plus $m$ in the range of from 20 to 3000 such that the molecular size of the composition substantially prevents the passage of molecules of the composition through the mucosa of the gastrointestinal tract when the composition is ingested.

21. The coloring composition of claim 20 wherein $n$ is from 0.4 to 2 times $m$.

* * * * *